Aug. 11, 1964 K. K. MESERVE Plant Pat. 2,434
ILEX (HOLLY) PLANT
Filed July 12, 1963
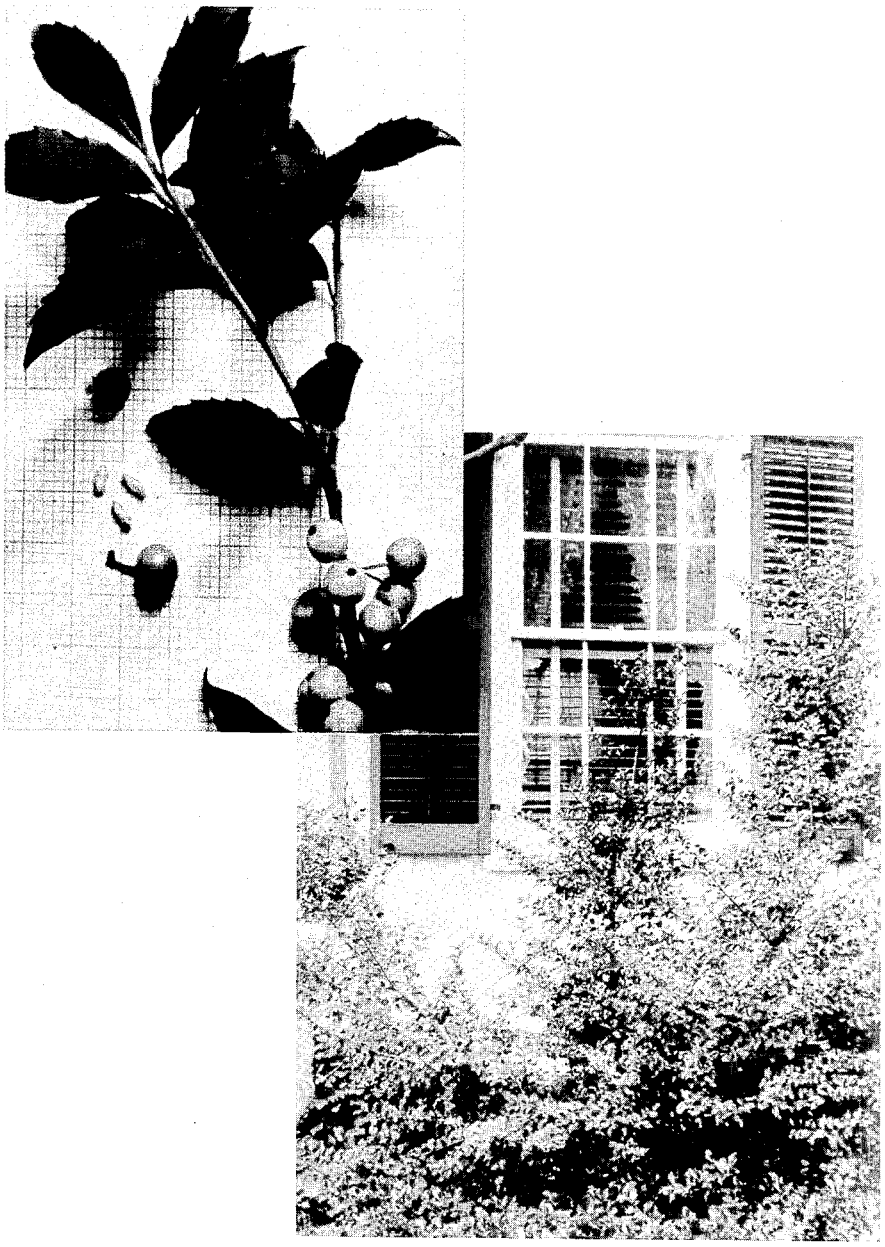
Inventor.
K. K. Meserve
By: Robb & Robb
Attorneys.

United States Patent Office

Plant Pat. 2,434
Patented Aug. 11, 1964

2,434
ILEX (HOLLY) PLANT

Kathleen K. Meserve, St. James, N.Y., assignor to Jackson & Perkins Company, Newark, N.Y., a corporation of New York Filed July 12, 1963, Ser. No. 294,780
1 Claim. (Cl. Plt.—65)

The present invention relates to the pistillate form of a new and distinct variety of Ilex (holly) plant which was originated by me by crossing an unnamed holly variety (unpatented) of the species botanically known as *"Ilex rugosa"* with another unname holly variety (unpatented) of the species botanically known as *"Ilex aquifolium."*

The primary objective of this breeding was to produce a new holly variety of the *"Ilex aquifolium"* class which which is a shrub and is more hardy and more suitable for the colder regions. This objective was fully achieved, along with other desirable improvements, as evidenced by the following unique combination of characteristics which are outstanding in the new variety and which distinguish it from its parents, as well as from all other varieties of which I am aware:

(1) A vigorous, upright and highly decorative shrub-like growth;

(2) Attractive red berries which ripen six weeks earlier than those of *"Ilex aquifolium"*;

(3) Unusually angled branches of Perilla Purple color;

(4) A distinctive and attractive over-all purple cast of the entire plant which is largely attributable to the purple colored angled branches; and (5) Good hardiness comparable to that of the species botanically known as *"Ilex crenata,"* yet being more decorative than the latter species.

Asexual reproduction of my new variety by cuttings, as performed at Shiloh, New Jersey, and also at St. James, Long Island, New York, shows that the foregoing characteristics and distinctions come true to form and are established and transmitted through succeeding propagations.

The accompanying drawing shows typical specimens of the wood, foliage and berries of my new variety in different stages of development and as depicted in color as nearly true as it is reasonably possible to make the same in a color illustration of this character, and also a black and white view of a typical specimen plant which shows its general habit of growth.

The following is a detailed description of my new variety, with color terminology in accordance with Ridgway's Color Standards and Nomenclature:

Type: Evergreen shrub with berries.
Class: Hybrid Ilex.
Parentage: Seedling.
*Seed parent.*—*"Ilex rugosa."*
*Pollen parent.*—*"Ilex aquifolium."*
Locality where grown and observed: St. James, Long Island, New York and Shiloh, New Jersey.
Habit of growth: Vigorous; upright; bushy.
Hardiness: Very hardy; withstands temperatures similar to *"Ilex crenata."*
Foliage:
*Leaves.*—Small in comparison with *"Ilex aquifolium,"* large in comparison with *"Ilex rugosa"*; from ovate to oblong-ovate; from 2 cm. to 4 cm. long; with acute wavy margin having from 3 to 7 pairs of triangular spiny teeth; alternate; short-petioled.
*Color.*—Upper side—Lustrous Dark Green, corresponding to Forest Green, Plate 17, with rugose surface on the upper side of the leaf. Under side—Deep Dull Yellow-Green (1), Plate 32.
Branches: Glabrous; angled. Color—Dark Purple, corresponding to Perilla Purple, Plate 37.
Flowers: 6 mm. or 7 mm. in diameter; short-stalked (from 3 mm. to 5 mm.); fascicled in axils of leaves on preceding year's branches. Pistillate flowers—borne singly and in clusters of 1 to 3 flowers, with superior ovary; color—White, Plate 53.
Fruit: A berry-like drupe; globose; from 6 mm. to 8 mm. in diameter. Color—Spectrum Red, Plate 1.

I claim:

A new and distinct variety of Ilex (holly) plant of the evergreen shrub type, substantially as herein shown and described, characterized particularly as to novelty by the unique combination of a vigorous, upright and highly decorative shrub-like growth, attractive red berries, unusually angled branches of Perilla Purple color, giving to the entire plant an over-all purple cast, and a very hardy habit comparable to that of the species *"Ilex crenata."*

No references cited.